US008946128B2

(12) United States Patent
Løset

(10) Patent No.: US 8,946,128 B2
(45) Date of Patent: Feb. 3, 2015

(54) SIGNAL SEQUENCE-INDEPENDENT PIX PHAGE DISPLAY

(75) Inventor: Geir Åge Løset, Oslo (NO)

(73) Assignee: Nextera AS, Oslo (NO)

( * ) Notice: Subject to any disclaimer, the term of this patent is extended or adjusted under 35 U.S.C. 154(b) by 80 days.

(21) Appl. No.: 13/201,334

(22) PCT Filed: Feb. 24, 2010

(86) PCT No.: PCT/EP2010/052344
§ 371 (c)(1), (2), (4) Date: Aug. 12, 2011

(87) PCT Pub. No.: WO2010/097411
PCT Pub. Date: Sep. 2, 2010

(65) Prior Publication Data

US 2011/0301064 A1 Dec. 8, 2011

Related U.S. Application Data

(60) Provisional application No. 61/155,437, filed on Feb. 25, 2009.

(30) Foreign Application Priority Data

May 28, 2009 (DK) .................................. 2009 0666

(51) Int. Cl.
*C40B 40/08* (2006.01)
*C12N 15/10* (2006.01)

(52) U.S. Cl.
CPC .................................. *C12N 15/1037* (2013.01)
USPC ............................................................ 506/17

(58) Field of Classification Search
None
See application file for complete search history.

(56) References Cited

U.S. PATENT DOCUMENTS

| | | | | |
|---|---|---|---|---|
| 7,037,706 | B1 | 5/2006 | Barrett et al. | |
| 2003/0162249 | A1* | 8/2003 | Gray et al. | 435/69.1 |
| 2003/0186322 | A1* | 10/2003 | Janda et al. | 435/7.1 |
| 2006/0068421 | A1 | 3/2006 | Gray | |
| 2006/0252028 | A1 | 11/2006 | Ueda | |
| 2011/0251106 | A1 | 10/2011 | Løset | |
| 2012/0201814 | A1* | 8/2012 | McKinnon et al. | 424/133.1 |

FOREIGN PATENT DOCUMENTS

| | | | |
|---|---|---|---|
| WO | WO 00/71694 | A1 | 11/2000 |
| WO | WO 2004/050871 | A1 | 6/2004 |

(Continued)

OTHER PUBLICATIONS

Score Report Janda et al SEQ ID No. 1 print date Mar. 20, 2013.*

(Continued)

*Primary Examiner* — Catherine Hibbert
(74) *Attorney, Agent, or Firm* — Knobbe Martens Olson & Bear LLP

(57) ABSTRACT

The present invention provides an alternative scaffold for peptides displayed on filamentous phages through novel fusion proteins primarily originating from pIX. Libraries of filamentous phages can be created from fusion proteins, and a phage display system comprising a phagemid and a helper phage is a part of the invention. An aspect of the invention is a kit containing a phage display system comprising a phagemid that contains a nucleic acid encoding the fusion protein of the invention and a helper phage.

10 Claims, 5 Drawing Sheets pVII
pVI
pIX
ssDNA
pVIII
CT N2 N1

(56) References Cited

FOREIGN PATENT DOCUMENTS

| | | | |
|---|---|---|---|
| WO | WO 2009/024591 | A1 | 2/2009 |
| WO | WO 2009/085462 | A1 | 7/2009 |

OTHER PUBLICATIONS

Simons et al (Proceedings of the National Academy of Sciences USA vol. 78 pp. 4194 to 4198, published Jul. 1, 1981).*

Kwaśnikowski, Piotr et al., "Multivalent display system on filamentous bacteriophage pVII minor coat protein" Journal of Immunological Methods, 2005, pp. 135-143, vol. 307.

Endemann, Heike et al., "Location of Filamentous Phage Minor Coat Proteins in Phage and in Infected Cells" J. Mol. Biol., 1995, pp. 496-506, vol. 250.

Gao, Changshou et al., "A method for the generation of combinatorial antibody libraries using pIX phage display" PNAS, Oct. 1, 2002, pp. 12612-12616, vol. 99, No. 20.

Gao, Changshou et al., "Making artificial antibodies: A format for phage display of combinatorial heterodimeric arrays" Proc. Natl. Acad. Sci., May 1999, pp. 6025-6030, vol. 96.

International Preliminary Report on Patentability for PCT/EP2010/052344 dated Aug. 30, 2011.

* cited by examiner

A.

B.

C.

D.

SEQUENCE LISTING

```
<160> NUMBER OF SEQ ID NOS: 11

<210> SEQ ID NO 1
<211> LENGTH: 32
<212> TYPE: PRT
<213> ORGANISM: Bacteriophage M13

<400> SEQUENCE: 1

Met Ser Val Leu Val Tyr Ser Phe Ala Ser Phe Val Leu Gly Trp Cys
1               5                   10                  15

Leu Arg Ser Gly Ile Thr Tyr Phe Thr Arg Leu Met Glu Thr Ser Ser
            20                  25                  30


<210> SEQ ID NO 2
<211> LENGTH: 4860
<212> TYPE: DNA
<213> ORGANISM: Artificial Sequence
<220> FEATURE:
<223> OTHER INFORMATION: Phagemid

<400> SEQUENCE: 2

tggcgtaata gcgaagaggc ccgcaccgat cgcccttccc aacagttgcg cagcctgaat      60

ggcgaatggg acgcgccctg tagcggcgca ttaagcgcgg cgggtgtggt ggttacgcgc     120

agcgtgaccg ctacacttgc cagcgcccta gcgcccgctc ctttcgcttt cttcccttcc     180

tttctcgcca cgttcgccgg ctttccccgt caagctctaa atcgggggct ccctttaggg     240
```

-continued

```
ttccgattta gtgctttacg gcacctcgac cccaaaaaac ttgattaggg tgatggttca    300
cgtagtgggc catcgccctg atagacggtt tttcgccctt tgacgttgga gtccacgttc    360
tttaatagtg gactcttgtt ccaaactgga acaacactca accctatctc ggtctattct    420
tttgatttat aagggatttt gccgatttcg gcctattggt taaaaaatga gctgatttaa    480
caaaaattta acgcgaattt taacaaaata ttaacgctta caatttaggt ggcacttttc    540
ggggaaatgt gcgcggaacc cctatttgtt tatttttcta aatacattca aatatgtatc    600
cgctcatgag acaataaccc tgataaatgc ttcaataata ttgaaaaagg aagagtatga    660
gtattcaaca tttccgtgtc gcccttattc cctttttttgc ggcattttgc cttcctgttt    720
ttgctcaccc agaaacgctg gtgaaagtaa aagatgctga agatcagttg ggtgcacgag    780
tgggttacat cgaactggat ctcaacagcg gtaagatcct tgagagtttt cgccccgaag    840
aacgttttcc aatgatgagc acttttaaag ttctgctatg tggcgcggta ttatcccgta    900
ttgacgccgg gcaagagcaa ctcggtcgcc gcatacacta ttctcagaat gacttggttg    960
agtactcacc agtcacagaa aagcatctta cggatggcat gacagtaaga gaattatgca   1020
gtgctgccat aaccatgagt gataacactg cggccaactt acttctgaca acgatcggag   1080
gaccgaagga gctaaccgct tttttgcaca acatggggga tcatgtaact cgccttgatc   1140
gttgggaacc ggagctgaat gaagccatac caaacgacga gcgtgacacc acgatgcctg   1200
tagcaatggc aacaacgttg cgcaaactat taactggcga actacttact ctagcttccc   1260
ggcaacaatt aatagactgg atggaggcgg ataaagttgc aggaccactt ctgcgctcgg   1320
cccttccggc tggctggttt attgctgata aatctggagc cggtgagcgt gggtctcgcg   1380
gtatcattgc agcactgggg ccagatggta agccctcccg tatcgtagtt atctacacga   1440
cggggagtca ggcaactatg gatgaacgaa atagacagat cgctgagata ggtgcctcac   1500
tgattaagca ttggtaactg tcagaccaag tttactcata tatactttag attgatttaa   1560
aacttcattt ttaatttaaa aggatctagg tgaagatcct ttttgataat ctcatgacca   1620
aaatccctta acgtgagttt tcgttccact gagcgtcaga ccccgtagaa aagatcaaag   1680
gatcttcttg agatcctttt tttctgcgcg taatctgctg cttgcaaaca aaaaaaccac   1740
cgctaccagc ggtggtttgt ttgccggatc aagagctacc aactcttttt ccgaaggtaa   1800
ctggcttcag cagagcgcag ataccaaata ctgtccttct agtgtagccg tagttaggcc   1860
accacttcaa gaactctgta gcaccgccta catacctcgc tctgctaatc ctgttaccag   1920
tggctgctgc cagtggcgat aagtcgtgtc ttaccgggtt ggactcaaga cgatagttac   1980
cggataaggc gcagcggtcg ggctgaacgg ggggttcgtg cacacagccc agcttggagc   2040
gaacgaccta caccgaactg agatacctac agcgtgagct atgagaaagc gccacgcttc   2100
ccgaagggag aaaggcggac aggtatccgg taagcggcag ggtcggaaca ggagagcgca   2160
cgagggagct tccaggggga aacgcctggt atctttatag tcctgtcggg tttcgccacc   2220
tctgacttga gcgtcgattt ttgtgatgct cgtcaggggg gcggagccta tggaaaaacg   2280
ccagcaacgc ggccttttta cggttcctgg ccttttgctg gccttttgct cacatgttct   2340
ttcctgcgtt atcccctgat tctgtggata accgtattac cgcctttgag tgagctgata   2400
ccgctcgccg cagccgaacg accgagcgca gcgagtcagt gagcgaggaa gcggaagagc   2460
gcccaatacg caaaccgcct ctccccgcgc gttggccgat tcattaatgc aggtatcacg   2520
aggccctttc gtcttcacct cgagagcggg cagtgagcgc aacgcaatta atgtgagtta   2580
gctcactcat taggcacccc aggctttaca ctttatgctt ccggctcgta tgttgtgtgg   2640
```

```
aattgtgagc ggataacaat ttcacacaga attcattaaa gaggagaaat taaccatgaa   2700
atacctattg cctacggcag ccgctggctt gctgctgctg gcagctcagc cggccatggc   2760
gcaagttcag ctgcagcagt ctggggctga actggtgagg cctggggtct cagtgaagat   2820
ttcctgcaag ggttctggct acaaattcac tgattatgct acgcactggg tgaaacagag   2880
tcatgcaaag agtctagagt ggattggagt tattagtact tactatggtg atactactta   2940
taaccagaag ttcaagggca aggccacaat gactgtcgac aaatcctcca gcacagccta   3000
tatggaactt cccagactga catctgatga ttctgccatc tattattgtg ccctgttacg   3060
cccctttgct tactggggcc aagggaccac ggtcaccgta tcctcaggga gtgcatccgc   3120
cccaaagctt gaagaaggtg aattttcaga agcacgcgta gatatcgtgc tgacccaatc   3180
tccactctcc ctgagtgtgt cagcaggaga gaaggtcact atgagctgca agtccagtca   3240
gagtctgtta aacagtggaa atcaaaataa cgacttggcc tggtaccagc agaaaccagg   3300
gcaacgtcct aaactgttga tctacggggc atccactagg gaatctgggg tccctgatcg   3360
cttcacaggc agtggatctg gaaccgattt cactcttacc atcagcagtg tgcaggctga   3420
agacctggca gtttattact gtcagaatga tcatagttat ccgttaacgt tcggtgctgg   3480
caccaagctg gaaatcaaac gggcggccgc tggatccaaa gatatcagag ctgaaactgt   3540
tgaaagttgt ttagcaaaat cccatacaga aaattcattt actaacgtct ggaaagacga   3600
caaaacttta gatcgttacg ctaactatga gggctgtctg tggaatgcta caggcgttgt   3660
agtttgtact ggtgacgaaa ctcagtgtta cggtacatgg gttcctattg ggcttgctat   3720
ccctgaaaat gagggtggtg gctctgaggg tggcggttct gagggtggcg gttctgaggg   3780
tggcggtact aaacctcctg agtacggtga tacacctatt ccgggctata cttatatcaa   3840
ccctctcgac ggcacttatc cgcctggtac tgagcaaaac cccgctaatc ctaatccttc   3900
tcttgaggag tctcagcctc ttaatacttt catgtttcag aataataggt tccgaaatag   3960
gcagggggca ttaactgttt atacgggcac tgttactcaa ggcactgacc ccgttaaaac   4020
ttattaccag tacactcctg tatcatcaaa agccatgtat gacgcttact ggaacggtaa   4080
attcagagac tgcgctttcc attctggctt taatgaggat ttatttgttt gtgaatatca   4140
aggccaatcg tctgacctgc ctcaacctcc tgtcaatgct ggcggcggct ctggtggtgg   4200
ttctggtggc ggctctgagg gtggtggctc tgagggtggc ggttctgagg gtggcggctc   4260
tgagggaggc ggttccggtg gtggctctgg ttccggtgat tttgattatg aaaagatggc   4320
aaacgctaat aagggggcta tgaccgaaaa tgccgatgaa aacgcgctac agtctgacgc   4380
taaaggcaaa cttgattctg tcgctactga ttacggtgct gctatcgatg gtttcattgg   4440
tgacgtttcc ggccttgcta atggtaatgg tgctactggt gattttgctg gctctaattc   4500
ccaaatggct caagtcggtg acggtgataa ttcaccttta atgaataatt tccgtcaata   4560
tttaccttcc ctccctcaat cggttgaatg tcgccctttt gtctttggcg ctggtaaacc   4620
atatgaattt tctattgatt gtgacaaaat aaacttattc cgtggtgtct ttgcgtttct   4680
tttatatgtt gccaccttta tgtatgtatt ttctacgttt gctaacatac tgcgtaataa   4740
ggagtcttaa tgatctagag gcctgtgcta atgatcagct agcttgaggc atcaataaaa   4800
cgaaaggctc agtcgaaaga ctgggccttt cgttttatct gttgtttgtc ggttaacgtc   4860
```

<210> SEQ ID NO 3
<211> LENGTH: 249
<212> TYPE: PRT

```
<213> ORGANISM: Artificial Sequence
<220> FEATURE:
<223> OTHER INFORMATION: fragment of scFv

<400> SEQUENCE: 3

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Tyr Gly Ser Ser Tyr Phe Asp Tyr Trp Gly Gln
            100                 105                 110

Gly Thr Thr Leu Thr Val Ser Ser Leu Glu Gly Gly Gly Gly Ser Gly
        115                 120                 125

Gly Gly Gly Ser Gly Gly Gly Gly Ser Glu Leu Gln Ala Val Val Thr
    130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Asn Arg Ala Pro Gly Val Pro Ala Arg Phe Ser Gly Ser Leu Ile
        195                 200                 205

Gly Asp Lys Ala Ala Leu Thr Ile Thr Gly Thr Gln Thr Glu Asp Glu
    210                 215                 220

Ala Met Tyr Phe Cys Ala Leu Trp Tyr Ser Asn His Trp Val Phe Gly
225                 230                 235                 240

Gly Gly Thr Lys Leu Thr Val Leu Gly
                245


<210> SEQ ID NO 4
<211> LENGTH: 22
<212> TYPE: PRT
<213> ORGANISM: Artificial Sequence
<220> FEATURE:
<223> OTHER INFORMATION: signal sequence

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala
            20


<210> SEQ ID NO 5
<211> LENGTH: 39
<212> TYPE: DNA
<213> ORGANISM: Artificial Sequence
<220> FEATURE:
<223> OTHER INFORMATION: Primer

<400> SEQUENCE: 5
```

agaggagaaa ttaaccatgg aatacctatt gcctacggc 39

<210> SEQ ID NO 6
<211> LENGTH: 39
<212> TYPE: DNA
<213> ORGANISM: Artificial Sequence
<220> FEATURE:
<223> OTHER INFORMATION: Primer

<400> SEQUENCE: 6
gccgtaggca ataggtattc catggttaat ttctcctct 39

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tagctcactc attaggcacc c 21

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
tttggatcca gcggccgc 18

<210> SEQ ID NO 9
<211> LENGTH: 40
<212> TYPE: DNA
<213> ORGANISM: Artificial Sequence
<220> FEATURE:
<223> OTHER INFORMATION: Primer

<400> SEQUENCE: 9
atatgatatc agaatgagtg ttttagtgta ttctttcgcc 40

<210> SEQ ID NO 10
<211> LENGTH: 39
<212> TYPE: DNA
<213> ORGANISM: Artificial Sequence
<220> FEATURE:
<223> OTHER INFORMATION: Primer

<400> SEQUENCE: 10
atatgctagc ttatcatgag gaagtttcca ttaaacggg 39

<210> SEQ ID NO 11
<211> LENGTH: 253
<212> TYPE: PRT
<213> ORGANISM: Artificial Sequence
<220> FEATURE:
<223> OTHER INFORMATION: scFv

<400> SEQUENCE: 11

Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Asn Tyr
            20                  25                  30

-continued

```
Gly Ile Thr Trp Val Arg Gln Ala Pro Gly Gln Gly Leu Glu Trp Met
        35                  40                  45

Gly Trp Ile Ser Ala Tyr Asn Gly Tyr Lys Ser Tyr Ala Gln Asn Phe
    50                  55                  60

Gln Gly Arg Val Thr Met Thr Thr Asp Thr Phe Thr Ser Thr Ala Tyr
65                  70                  75                  80

Met Glu Leu Arg Thr Leu Arg Ser Asp Asp Thr Ala Val Tyr Tyr Cys
                85                  90                  95

Val Arg Leu Val Pro Lys Arg Thr Ala Thr Leu His Tyr Tyr Ile Asp
            100                 105                 110

Val Trp Gly Lys Gly Thr Thr Val Thr Val Ser Ser Gly Ser Ala Ser
        115                 120                 125

Ala Pro Lys Leu Glu Glu Gly Glu Phe Ser Glu Ala Arg Val Gln Ser
    130                 135                 140

Val Leu Thr Gln Pro Pro Ser Val Ser Ala Ala Pro Gly Gln Lys Val
145                 150                 155                 160

Thr Ile Ser Cys Ser Gly Ser Ser Ser Asn Ile Gly Asn Asn Tyr Val
                165                 170                 175

Ser Trp Tyr Val Gln Leu Pro Gly Thr Ala Pro Lys Leu Leu Ile Tyr
            180                 185                 190

Asp Asn Asn Lys Arg Phe Ser Gly Val Pro Asp Arg Phe Ser Gly Ser
        195                 200                 205

Lys Ser Gly Thr Ser Ala Thr Leu Gly Ile Thr Gly Leu Gln Thr Gly
    210                 215                 220

Asp Glu Ala Asp Tyr Tyr Cys Gly Ala Trp Asp Gly Ser Leu Arg Glu
225                 230                 235                 240

Ala Val Phe Gly Gly Gly Thr Lys Val Thr Val Leu Gly
                245                 250
```

SIGNAL SEQUENCE-INDEPENDENT PIX PHAGE DISPLAY

CROSS REFERENCE TO RELATED APPLICATIONS

This application claims the benefit and priority to and is a U.S. National Phase Application of PCT International Application Number PCT/EP2010/052344, filed on Feb. 24, 2010, designating the United States of America and published in the English language, which is an International Application of and claims the benefit of priority to U.S. Provisional Application No. 61/155,437, filed on Feb. 25, 2009, and Danish Patent Application No. PA 2009 0666, filed on May 28, 2009. The disclosures of the above-referenced applications are hereby expressly incorporated by reference in their entireties.

BACKGROUND OF THE INVENTION

The use of combinatorial approaches for protein identification, characterization and modification has been highly successful in both academic and commercial research and development. In this respect, filamentous bacteriophage, or phage, display technology has paved the way being the first library platform and still thrones as the dominating technology. Thus, phage display is widely applied in both basic and applied protein discovery, as well as in development of both novel protein-based diagnostics and therapeutic, which are the class of compounds most rapidly growing world-wide.

The principle of combinatorial phage display technology is based on the genotype-phenotype linkage offered by the property that each virion will only display on its surface the very same proteins that are encoded by the genome encapsulated by its protein coat. The phage particle itself is highly resistant to a variety of physiochemical conditions; hence phage display offers superior versatility in many selection regimes as compared to competing combinatorial technologies.

Phage display of heterologous polypeptides has been achieved using all five structural proteins of the filamentous phage coat, but only pIII- and to some extent pVIII-display have gained widespread use (FIG. 1).

When the heterologous fusion is only a short peptide, multivalent display systems using phage genome-based vectors are preferred, whereas for larger fusions requiring folded domains most applications will benefit from phagemid systems. In the latter case, antibody-pIII phage display is by far dominating the field, but alternative scaffolds are emerging at dawns early light, continuing the need for expansion of protein engineering tools of tomorrow. A highly desired application is to effectively obtain high affinity specific peptide or protein binders from a phage display library simply by infecting bacteria with phage virions while still bound to its target.

Endemann and Model, 1995 (PMID: 7616570), reported that the minor coat pIX was not functional with another protein fused to its N-terminus. Therefore, this report concluded that pIX cannot be used for phage display.

Both Gao et al. (PMID: 10339535, 12239343 and WO0071694) and Khalil et al. (PMID: 17360403) have later shown that N-terminal pIX fusion display is allowed when expressed from phagemids and used in combination with signal sequence-dependent periplasmic targeting. In these systems, complementation takes place as wt pIX is donated from the helper phage genome upon phagemid rescue.

The phagemid as disclosed in FIG. 2A of WO0071694 (without fusion protein inserted) and FIG. 2B of WO0071694 (with fusion protein inserted) clearly comprises a pelB signal sequence (with figure text on page 7, lines 2-14).

As mentioned above, it had previously been suggested that pIX was not functional with another protein fused to the N termini, and Gao et. al. gave two possible reasons for their success, either alone or by the combination of both.

One possible reason was that a prokaryotic leader sequence (signal sequence) was attached N-terminally to the fusion proteins, thus ensuring targeting of the recombinant protein to the periplasmic space and thereby prevented accumulation in the cytoplasm.

Another possible reason was that the recombinant proteins were expressed from a phagemid, not a phage genome as by Endemann and Model, hence wild type pIX from the helper phage inevitably needed for phagemid rescue were complementing the recombinant pIX fusion proteins, thus preserving wild type functionality that otherwise may have been lost due to the recombinant modification. I.e. the phages would comprise a mix of wild-type and fusion proteins.

Khalil et al. (PMID: 17360403) describes an application exploiting the feature of a bispecific filamentous phage virion in which an exogenous peptide is displayed at each distal tip of the very same virion. They achieved this by using the combination of a common pIII phage genome vector complementing a prokaryotic signal sequence dependent pIX display phagemid. In this setting, the phage genome vector served as a helper phage in rescuing the phagemid.

SUMMARY OF THE INVENTION

An object of the present invention is to provide an alternative scaffold for peptides displayed on filamentous phages.

A first aspect of the invention is a pIX fusion proteins originating from a filamentous phage, said fusion proteins does not comprise a prokaryotic N-terminal signal sequence and hence is a direct fusion to an exogenous peptide.

Another aspect of the invention relates to nucleic acids encoding the fusion proteins of the invention.

One aspect of the invention relates to filamentous phages comprising the fusion proteins of the invention.

Another aspect of the invention relates to a library of filamentous phages.

Another aspect of the invention relates to a phage display system comprising a phagemid and a helper phage, wherein the phagemid comprises a nucleic acid encoding the pIX fusion proteins of the invention.

One aspect relates to a kit comprising a phage display system comprising a phagemid and a helper phage, wherein the phagemid comprises a nucleic acid encoding the pIX fusion proteins of the invention.

Figure 1:
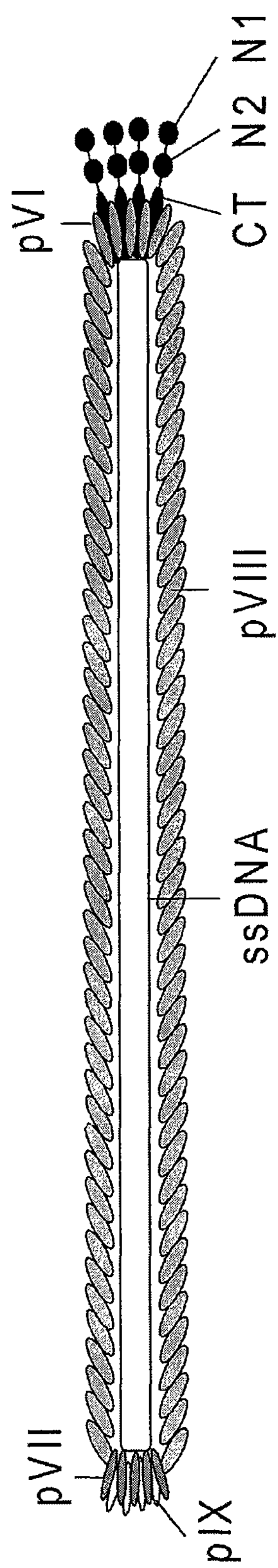
FIG. 1.

Schematic drawing of the filamentous phage structure. The virion is built up by five structural proteins that coat a single-stranded DNA molecule. In the wild type (wt) phage there are about 2700 copies of pVIII and approximately 3-5 copies of either of the four proteins pIII, pVI, pVII and pIX, which are found at each tip of the virion. Virion size is dependent on the genome size at approx. 2.3 nucleotides per pVIII coat protein and thus the length of the particle is accommodated by an increase or decrease in the inserted copies of pVIII. Notably, the pIII and pVIII structures have been characterized by x-ray fiber diffraction, crystallography and NMR. The minor coat protein pIII contains three distinct domains separated by glycin-rich regions: N1 (binds to TolA), N2 (binds to the F pilus) and CT (integrated into the virion and is important for normal virion assembly).

FIG. 2

Schematic drawings of the novel pGALD9 (A) and pGALD97ΔL (B) pIX display phagemids. The vector backbone of both phagemids was based on the pIII display phagemid pSEX81 (SEQ ID NO:2), which sequence can be accessed from GenBank accession no.: Y14584, and details on the constructed are described in Material and Methods. Both phagemids can accommodate segments of in frame exogenous sequences (termed $E_1$ and $E_2$) through easy cassette exchange of the NcoI/HindIII and MluI/NotI portions respectively. The cassettes are connected by a synthetic linker sequence that varies among the different constructs described herein. Abbreviations: lacPO, lac promoter; sd, Shine-Dalgarno sequence; pelB, signal sequence of bacterial pectate lyase; TP, trypsine protease site; t, T7 transcriptional terminator.

FIG. 3

Phagemid titers of (A) scFv anti-phOx (SEQ ID NO:11) and (C) scFv anti-NIP displayed from pGALD9ΔL, pGALD9, pSEX81.

All the phagemids harbour an ampicillin resistance marker; hence the titers are shown as ampicillin resistant colony forming units per millilitre solution ($cfu^{ampR}$/ml). Phagemid to helper phage ratios of (B) scFv anti-phOx (SEQ ID NO:11) and (D) scFv anti-NIP displayed from pGALD9ΔL, pGALD9, pSEX81 shown as the ratio of the phagemid titer ($cfu^{ampR}$/ml) divided by helper phage titer ($cfu^{kanR}$/ml). The virion packaging was done by standard phagemid rescue as described in materials and methods without (basal expression), or with a final concentration of 0.1 mM IPTG present (IPTG induction) after super infection.

FIG. 4

Antigen specific ELISA comparing functional (A) scFv anti-phOx (SEQ ID NO:11) and (B) scFv anti-NIP (SEQ ID NO: 3) display between pIX and pIII, and with and without signal sequence (ΔL). The ELISA was conducted as described in materials and methods using 100 μl/well cleared virion-containing supernatant. The anti-$M13^{HRP}$ is a negative control on unspecific adsorption of the virion detection MAb to the antigen and block. (C and D) The ELISA in A and B were repeated, but development was stopped before signal saturation and the relative display levels determined using antigen reactivity as a function of titer.

FIG. 5

Apparent target-specific enrichment in affinity selection depends on capsid display scaffold, expression of Protein of Interest (POI) and elution conditions. Equal volumes of untitrated virion-containing supernatant from each of the 8 phOx-/NIP-spiked libraries after selection round 1 and 2 were assessed for antigen reactivity by ELISA. Round 0 corresponds to the spiked input of $1\times10^{10}$ $cfu^{ampR}$. To estimate maximum possible response, clonal supernatants from which the spiked concentrates in round 0 were derived were included and the results depicted are given by background subtracted signals as fraction of the maximum possible response indicated by cone shape.

DETAILED DESCRIPTION OF THE INVENTION

It should be noted that embodiments and features described in the context of one of the aspects of the present invention also apply to the other aspects of the invention.

All patent and non-patent references cited in the present application, are hereby incorporated by reference in their entirety.

We here present a novel concept, in which the structural coat protein pIX of the filamentous phage virion is genetically altered such that the modified version encodes an N-terminal peptide or protein domain.

pIX Fusion Protein

In one aspect, the present invention provides a pIX fusion protein originating from a filamentous phage, said fusion protein comprising a fusion of an exogenous peptide to the N-terminus of pIX. Such a fusion protein is useful e.g. in the context of phage display.

When referring to an exogenous peptide, what is meant is a peptide not originally part of the pIX protein with or without any linker amino acids to the N-terminal end of the pIX amino acid part of the fusion protein.

In a preferred embodiment, the nucleic acid encoding the fusion protein does not comprise a prokaryotic N-terminal signal sequence.

As used herein, the term peptide encompasses both short peptides, polypeptides, proteins and fragments thereof.

The term pIX protein refers to the amino acid sequence disclosed in (SEQ ID NO 1 (MSVLVYSFASFVLGWCLRSGITYFTRLMETSS)

In an embodiment the pix protein comprises the amino acid with a sequence identity of at least 70% to that of SEQ ID NO 1, such as 75% identity, such as 80% identity, such as 81% identity, such as 82% identity, such as 83% identity, such as 84% identity, such as 85% identity, such as 86% identity, such as 87% identity, such as 88% identity, such as 89% identity, such as 90% identity, such as 91% identity, such as 92% identity, such as 93% identity, such as 94% identity, such as 95% identity, such as 96% identity, such as 97% identity, such as 98% identity, such as 99% identity.

Sequence Identity

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. “scoring matrix” and “gap penalty” may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

Folded Proteins

In a preferred embodiment, the term peptide refers exclusively to folded proteins such as antibody derived domains. The skilled addressee would recognise folded proteins could be antibodies or fragments thereof, covering Fv, scFv, Fab, single domains, Z domain of protein A or fragments thereof (Affibody), Ankyrin or fragments thereof, DARPin or fragments thereof, T cell receptor or fragments thereof, MHC class I or II or fragments thereof, Fibronectin or fragments thereof, Anticalins or fragments thereof, PDZ-domains or fragments thereof, IgNAR or fragments thereof, CTLA4 or fragments thereof, ImmE7 or fragments thereof, Knottins or fragments thereof, avimer or fragments thereof, GFP or fragments thereof and other gene-encoded biological fluorophores.

In principle, one can make a library of anything as long as it is displayed, hence in its simplest form one can only separate between something that has a non-structured configuration, as compared to an ordered structure, that is a fold.

In another preferred embodiment, the term peptide refers exclusively to short peptides between 2 to 50 aa. At some length a short random coil peptide will be long enough to adopt a defined secondary or tertiary fold and hence enter the folded domain definition. Obviously this will depend on chemical composition, hence one peptide of 20 aa will still be random coil, whereas another 20 aa peptide could be folded and fall into the folded domain definition.

In another preferred embodiment, the pIX fusion protein of the invention comprises a sequence selected from the group consisting of position 1-32, 2-32, 3-32, 4-32, 5-32, 6-32, 7-32, 8-32, 9-32, 10-32, 11-32 and 12-32 of SEQ ID NO:1. In principle, in a phagemid context, any N-terminal modification of pIX may be envisioned given that the transmembrane portion is retained and allows for normal virion incorporation and assembly.

SEQ ID NO:1 (MSVLVYSFASFVLGWCLRSGITYFTRLMETSS) is the amino acid sequence of structural coat protein pIX of the filamentous phage (wild type pIX). Most preferably, the pIX fusion protein comprises positions 1-32 of SEQ ID NO:1.

SEQ ID NO:1 should not be confused with a signal/leader sequence which is described below.

Signal Sequence

Preferably, the exogenous peptide is fused directly with or without any linker amino acids to the N-terminal end of the pIX sequence of the fusion protein.

In yet another preferred embodiment, the pIX fusion protein does not comprise a prokaryotic N-terminal leader sequence.

The term “leader sequence” is used interchangeably with the terms “signal peptide” and “signal sequence”, and refers to an amino acid sequence that targets the protein (of which the leader sequence is part) to the periplasmatic membrane space of gram negative bacteria. Examples of leader sequences often used are pelBss, OmpAss, TorAss, malEss, phoAss, lamBss, Blass, and DspAss, mglBss, sfmCss, tolBss and TorTss. Such signal sequences are known to target the complete protein to the secretory machinery of *E. coli* which is known to include at least SRP-dependent, SEC-dependent, TatABC-dependent or YidC-dependent translocation from the cytosol to the periplasmic space (Baneyx et al. PMID: 15529165). Hence, the term N-terminal signal sequence refers to a signal sequence that is in the N-terminal part of the protein.

Signal sequences harbouring the property of targeting a protein (of which it is part) to the secretory machinery of *E. coli* and thereby translocate it from the cytosolic to the periplasmic compartment can be partly identified through signatures, or motifs, defined by the chemical property of their amino acid composition.

The variety of functional signal sequence existing is as of yet, however, exceeding the current knowledge in identifying them, hence current state of the art in defining a peptide as a cognate signal sequences are typically done through data mining using knowledge based data based as template by e.g. neural network or heuristic methodology. There are several such tools available to the community through open access channels as of today, such as SignalP, PPSEARCH of PROSITE (EMBL-EBI), SecretomeP, TatP.

The challenge is even larger with the class of secretory proteins, in the sense that they are exported from the cytosolic compartment, that deviate from the rules such that no signal sequence motif can be identified, but through data mining one can also here define signal sequence features or get the probability of the secretory capacity of the eukaryotic protein in question. As of yet, no such tool exist for the prokaryotic taxa.

The only method currently available that irrevocably identified a peptide as a signal sequence is therefore by experimental means to validate the property of a peptide to establish whether or not it is a real signal sequence. It is also clear that engineering may be performed in such peptides such that the given amino acid positions in the signal sequence may be altered, yet retain its function as a signal peptide, either by native functionality, or by altered functionality, such as increased transport capacity. Also deletion or addition of amino acids may be employed. Such analysis and engineering have indeed been done with the Ff pVIII signal sequence, g8 pss targeting the Sec-pathway, and the TorAss targeting the Tat-pathway. Especially the results of Shen et al may serve as well-founded guide lines for engineering of functional, but altered mutants, of the pIII signal sequence and the bacterial pectate lyase signal sequence.

The functionality of a signal sequence may be further broken down into the two following properties:

1. Targeting a protein (of which it is part) to the secretory machinery of *E. coli* and thereby translocate it from the cytosolic to the periplasmic compartment and in the course of this process, being proteolytically separated from the remaining protein by specific proteases, such as Lipoprotein signal peptidase, or leader peptidases.

2. Targeting a protein (of which it is part) to the secretory machinery of *E. coli* and thereby translocate it from the cytosolic to the periplasmic compartment and after translocation still remain as a part of the protein.

Though the vast majority of signal sequences map to situation 1) given above, it is clear that these proteins may be easily engineered into situation 2). Therefore, any currently known signal sequences e.g. a mutant pelBss and other that originally belong to the situation 1), but are altered into situation 2), are still regarded as cognate signal sequences.

Moreover, it is conceivable to either alter a signal sequence of situation 1) into situation 2), or directly choose a signal sequence that map to situation 2) and then after translocation remove the signal sequence. This can be done either by endogenous proteases of the host and/or in the case of e.g. phage display, when the protein is fused to a capsid protein. One would then engineer into the proper region of the signal sequence, or the protein of which it is a part, an artificial protease site, such that a defined cleavage can be performed. On can here envision two different types of protease sites chosen:

A. The protease site does not cleave the protein of interest, only the predicted site, such as e.g. carboxypeptidase A, or 3C rhinovirus protease site in combination with antibodies or other scaffolds of interest, such as major histocompatibility complex molecules or T cell receptors. By using this approach one can envision e.g. phage display of the protein of interest by use of a signal sequence mapping to the situation 2) above and before used in selection etc, artificially remove the signal peptide to obtain functionality and homogeneity to the capsid fusion.

B. The protease site cleaves the protein of interest in addition to the engineered site, such as e.g. trypsin.

Both situations will still be regarded as signal sequence-dependent phage display.

Exogenous Peptide

In a preferred embodiment, the exogenous peptide of the pIX fusion protein is selected from the group consisting of antibodies or fragments thereof, covering Fv, scFv, Fab, single domains, Z domain of protein A or fragments thereof (Affibody), Ankyrin or fragments thereof, DARPin or fragments thereof, T cell receptor or fragments thereof, MHC class I or II or fragments thereof, Fibronectin or fragments thereof, Anticalins or fragments thereof, PDZ-domains or fragments thereof, IgNAR or fragments thereof, CTLA4 or fragments thereof, ImmE7 or fragments thereof, Knottins or fragments thereof, avimer or fragments thereof, GFP or fragments thereof and other gene-encoded biological fluorophores.

In a preferred embodiment, the exogenous peptide of the pIX fusion protein is a library member.

A library as used in the present context refers to a collection of different peptides. The peptides may be folded domains or short peptides of e.g. 2-50 amino acids. Such libraries are of interest because they can be used to identify new ligands binding to a given target.

There are several advantages of using pIX for displaying a library as compared to libraries displayed using pIII or pVIII. pIX display contains the same assets as pIII display with respect to directionality and valence, but will not affect infectivity, a phenomenon known to occur with pIII display, which introduces uncontrolled and unwanted heterogeneity into the system upon e.g. rescue after affinity selection.

Moreover, pIX display may be achieved without the need of a prokaryotic N-terminal signal sequence, which are prerequisites for both pIII and pVIII display. Finally, any target immobilised species in pIII display normally requires disruption (normally by competitive, or high or low pH elution) of this target-phage bond. This is e.g. known to severely hamper retrieval of high-affinity, or stable binders in pIII display. As pIII required for infection is unaltered and readily available for alternative interactions in pIX display even after phage-target interaction, this completely eliminates the need for bond disruption, e.g. acidic elution, as immobilised phages retain full infectivity and hence may be retrieved simply by infection whilst bound to target.

Nucleic Acid

A second aspect of the invention is a nucleic acid encoding the fusion protein of the invention. The nucleic acid of the invention may be part of a plasmid, a vector, a phage genome, a phagemid or a phasmid.

The term nucleic acid refers to a macromolecule composed of chains of monomeric nucleotides. In biochemistry these molecules carry genetic information or form structures within cells. The most common nucleic acids are deoxyribonucleic acid (DNA) and ribonucleic acid (RNA). In addition, the term nucleic acids include artificial nucleic acids such as peptide nucleic acid (PNA), Morpholino and locked nucleic acid (LNA), as well as glycol nucleic acid (GNA) and threose nucleic acid (TNA). Each of these is distinguished from naturally-occurring DNA or RNA by changes to the backbone of the molecule.

A phagemid or phasmid is a type of cloning vector developed as a hybrid of the filamentous phage Ff and plasmids to produce a vector that can propagate as a plasmid, and also be packaged as single stranded DNA in viral particles. Similarly to a plasmid, a phagemid can be used to clone DNA fragments and be introduced into a bacterial host by a range of techniques (transformation, electroporation). However, infection of a bacterial host containing a phagemid with a 'helper' phage, for example VCSM13 or M13K07, provides the necessary viral components to enable single stranded DNA replication and packaging of the phagemid DNA into phage particles.

Thus, one aspect of the present invention relates to a phage genome or a phagemid comprising a nucleic acid encoding a pIX fusion protein originating from a filamentous phage, wherein the fusion protein does not comprise a prokaryotic N-terminal signal sequence.

In embodiment of the present invention, the phage genome or phagemid comprises a nucleic acid encoding a pIX fusion protein originating from a filamentous phage, wherein the fusion protein does not comprise a prokaryotic N-terminal signal sequence and wherein the pIX fusion protein comprises a sequence selected from the group consisting of position 1-32, 2-32, 3-32, 4-32 and 5-32 of SEQ ID NO:1 (MSVLVYSFASFVLGWCLRSGITYFTRLMETSS).

In another embodiment of the present invention is the exogenous peptide fused directly to the N-terminal end of the pIX sequence.

An embodiment of the present invention relates to a phage genome or phagemid of the present invention, wherein the exogenous peptide fused to pIX is selected from the group consisting of antibodies or fragments thereof, covering Fv, scFv, Fab, single domains, Z domain of protein A or fragments thereof (Affibody), Ankyrin or fragments thereof, DARPin or fragments thereof, T cell receptor or fragments thereof, MHC class I or II or fragments thereof, Fibronectin or fragments thereof, Anticalins or fragments thereof, PDZ-domains or fragments thereof, IgNAR or fragments thereof, CTLA4 or fragments thereof, ImmE7 or fragments thereof, Knottins or fragments thereof, avimer or fragments thereof, GFP or fragments thereof and other gene-encoded biological fluorophores.

In another embodiment of the present invention is the exogenous peptide fused to pIX a library member.

Filamentous Phage

A third aspect of the invention is a filamentous phage comprising the fusion protein of the invention. The filamentous phage virion may harbour a phagemid.

Phage, often called bacteriophage, is here meant as a virus infecting, replicating and which is secreted from bacteria. A filamentous bacteriophage, or filamentous phage, is a phage with a single stranded DNA molecule (ssDNA) which is packaged with phage coat proteins. The secreted filamentous phage particle has phenotypically a filamentous structure.

The term filamentous phage as used herein encompasses both phage genome-derived virions and phagemid-derived virions.

The term helper phage refers to a virus which helps a separate and unrelated defective virus defined as e.g. a phagemid which in itself is not a phage genome neither a functional virus, but merely a plasmid containing one or several elements derived from a phage genome, to reproduce by infecting the same host cell that is already occupied by the defective virus and providing the proteins which the defective virus are missing and need to form virions containing the phagemid.

In one embodiment, the filamentous phage does comprise a nucleic acid encoding the fusion protein of the invention. Particular preferred is a phage that comprises a phagemid comprising the nucleic acid encoding the fusion protein of the invention.

A phage library is a collection of filamentous phages displaying peptides or proteins as part of one or more of the filamentous phage coat proteins. Such libraries can comprise two or more phages displaying different peptides or proteins.

Thus, in an embodiment of the present invention, the filamentous phages are displaying peptides or proteins as part of one or more of the filamentous phage coat proteins.

In an embodiment the filamentous phage further comprises a pIII fusion protein, a pVII fusion protein or a pVIII fusion protein.

An aspect of the invention is a library of filamentous phages of the invention, said filamentous phages displaying exogenous peptides or proteins as fusions to one or more of pIII, pVII, pVIII or pIX.

A library is a collection of filamentous phages displaying peptides or proteins as part of one or more of the filamentous phage coatproteins.

Such libraries can comprise two or more phages displaying different peptides or proteins.

An aspect of the present invention relates to a phage library comprising two or more filamentous phages displaying different proteins wherein at least one of these proteins is the pIX fusion protein expressed from the phage genome or a phagemid of the present invention.

An embodiment of the present invention relates to a phage library comprising two or more filamentous phages displaying different peptides or proteins.

In a particular embodiment is at least one of these peptides or proteins the pIX fusion protein of the invention.

In an embodiment, peptides are displayed simultaneously at pIX and either pIII, pVII or pVIII.

In another embodiment, peptides are displayed simultaneously at pIX and two or three selected form the group consisting of pIII, pVII or pVIII.

The term wild type, sometimes written wildtype, wild-type or wt, is the typical form of an organism, strain, gene, or characteristic as it occurs in nature. Wild type refers to the most common phenotype in the natural population. Wild type also refers to the allele at each locus required to produce the wild-type phenotype. Wild type is the standard of reference for the genotype and phenotype. In biology it relates specifically to the difference between a naturally occurring organism, and one that has been deliberately mutated. Site-directed mutagenesis is a research technique that allows for the mutation of specific nucleotides in the gene sequence of a wildtype gene. Wildtype proteins are written as wt-(name of protein) e.g. a wildtype pIX protein is written wt pIX, wt-pIX or wildtype pIX.

Thus, one aspect of the invention relates to the filamentous phage of the present invention that does not comprise a gene encoding wt pIX and/or the wt pIX protein.

Another aspect of the present invention relates to the filamentous phage of the invention that further comprises a gene encoding wt pIX and/or the wt pIX protein.

Another aspect of the present invention relates to a filamentous phage comprising a phage genome or phagemid of the present invention.

In an embodiment of the present invention, the filamentous phage comprising a phage genome or phagemid of the present invention, further comprises a gene encoding wt pIX and/or the wt pIX protein.

In another embodiment of the present invention, the filamentous phage comprising a phage genome or phagemid of the present invention, does not comprise a gene encoding wt pIX and/or the wt pIX protein.

A further aspect of the present invention relates to pIX fusion proteins that are functional in a phage display without complementation by wt pIX protein. An aspect of the present invention relates to a filamentous phage comprising a phage genome or phagemid of the present invention, further comprising one or more the group selected from pIII fusion protein, pVII fusion protein and pVIII fusion protein.

Phage Display System

A fifth aspect of the invention is a phage display system comprising a phagemid and a helper phage, wherein the helper phage comprises a nucleic acid encoding the pIX fusion protein of the invention.

Phage display system, phage display technique, phage display technology or simply phage display refers to a method for the discovery and study of protein-protein, protein-peptide, and protein-DNA interactions that utilizes bacteriophage to connect proteins with the genetic information that encodes them.

Displaying protein or displayed protein refers to a protein fused to a phage coat protein that is accessible for detection or immobilisation by a ligand.

A sixth aspect of the invention is a phage display system comprising a phagemid and a helper phage, wherein the phagemid comprises a nucleic acid encoding the pIX fusion protein of the invention.

An aspect of the present invention relates to a phage display system comprising a phage genome or phagemid of the present invention.

Another aspect of the present invention relates to a phage display system comprising a phage genome or phagemid of the present invention, and a helper phage, An aspect of the present invention relates to a phage library comprising two or more filamentous phages displaying different proteins wherein at least one of these proteins is the pIX fusion protein expressed from the phage genome or a phagemid of the present invention.

In an embodiment of the present invention comprises the phage library of the present invention one or more additional fusion proteins selected from pIII fusion protein, pVII fusion protein and pVIII fusion protein.

Kits

A seventh aspect of the invention is a kit comprising a phage display system composed of a phagemid and a helper phage, wherein the phagemid comprises the nucleic acid encoding the pIX fusion protein of the invention. The kit should include a phagemid with a pIX encoding gene with a multiple cloning site N-terminally in the coding region and a helper phage (e.g. M13K07, VCSM13 or other). The kit should be supplemented with protocols for infection, expression, immobilisation, selection and detection of phage clones. The kits should also be accompanied with necessary recipes for buffers and media for performing the specific assays.

A kit is here referred to a collection of reagents for generating phage particles with a single or bispecific fusion proteins either as a phage display library or as single phage particle. A kit could include phagemids, helper phages, bacterial strains and protocol with recipes for reagents and assay description. A kit can be used for the development of research, diagnostic and therapeutic reagents.

An aspect of the present invention relates to a kit comprising the phage display comprising a phage genome or phagemid of the present invention, and a helper phage, Another aspect of the present invention relates to a kit comprising the phage genome or phagemid of the present invention.

Yet another aspect of the present invention relates to a kit comprising a filamentous phage comprising the phage genome or phagemid of the present invention.

The invention will now be described in further details in the following non-limiting examples.

EXAMPLES

Example 1

Phagemid Display on pIX

Reagents

All media and buffers were prepared essentially as described in Sambrook et al. (2001) Molecular Cloning: A Laboratory Manual. Cold Spring Harbor, N.Y.: Cold Spring Harbor Laboratory Press. The anti-M13-HRP antibody was purchased from GE Healthcare Bio-Sciences AB (Uppsala, Sweden). Restriction enzymes (RE) were purchased from New England Biolabs (Ipswich, Mass., USA) with the exception of DpnI, which was obtained from Stratagene (LaJolla, Calif., USA). DNA oligos were purchased from MWG Biotech AG (Ebersberg, Germany). Bovine serum albumin (BSA) and Tween 20 was purchased form Sigma-Aldrich (Oslo, Norway). Pfu Turbo DNA polymerase was purchased from Stratagene (LaJolla, Calif., USA). The haptens 2-phenyloxazol-5-one (phOx) and 5-nitrophenacetyl (NIP) conjugated to BSA were prepared essentially as described elsewhere (Näkelä et al, PMID; 722243 and Michaelsen et al, PMID: 2125362). Isopropyl-beta-D-thiogalactopyranoside (IPTG) was purchased from Fermentas (Burlington, Canada). Triethylamine (TEA) and Trypsin/EDTA were purchased from Sigma-Aldrich (Oslo, Norway) and BioWhittaker (Lonza Group Ltd., Visp, Switzerland), respectively. The *E. coli* strain XL1-Blue was purchased from Stratagene (LaJolla, Calif., USA). M13K07 helper phage was purchased from GE Healthcare Bio-Sciences AB (Uppsala, Sweden). The pSEX81 (SEQ ID NO:2) phagemid (pIII display) harbouring a single chain Fv (scFv) with specificity against phOx-BSA was kindly provided by Affitech AS (Oslo, Norway). The prokaryotic expression vector pSG1 harbouring the scFv anti-NIP (SEQ ID NO: 3)(unpublished) is based on pHOG21 (Kiprianov et al, PMID: 9005945) and has been made in-house from the antibody variable genes derived from pLNOH2 and pLNOK (Norderhaug et al, PMID: 9202712).

Construction of the novel pIX display phagemid vectors pGALD9 and pGALD9ΔL As a starting template for the vector backbone, the pSEX81 (SEQ ID NO:2) phagemid described above was chosen (GenBank accession no.: Y14584). Firstly, to remove the prokaryotic pelB signal sequence (N-MKYLLPTAAAGLLLLAAQPAMA-C) (SEQ ID NO:4) encoding stretch in this vector, a NcoI RE site was introduced in the extreme N-terminus by QuikChange™ in vitro mutagenesis using the primer pair a41g-frwd/a41g-rev (5'-AGAGGAGAAATTAACCATGGAATAC-CTATTGCCTACGGC-3'/5-GCCGTAGGCAATAGGTAT-TCCATGGTTAATTTCTCCTCT-3') (SEQ ID NO:5 and SEQ ID NO: 6, respectively), thereby changing the first nucleotide in the second codon of the pelB ORF from A to G. Following mutagenesis, the vector was NcoI digested, religated and used as template in a second PCR retrieving the relevant part of the vector using the primer pair pHOG_EcoRI_frwd/scTCR_rev (5'-TAGCTCACTCATT-AGGCACCC-3'/5'-TTTGGATCCAGCGGCCGC-3') (SEQ ID NO:7 and SEQ ID NO: 8, respectively). This PCR fragment was then moved into the original pSEX81(SEQ ID NO:2) on the compatible EcoRI/HindIII RE sites using standard techniques and confirmed by DNA sequencing. This step completely removed the pelB signal sequence encoding portion, but preserved the start codon and its relative position towards the lacPO and Shine-Dalgarno sequence (SD) important for normal transcription and translation, as well as adding only one Ala residue before the exogenous sequence defined by the NcoI/NotI RE sites found in the original pSEX81 (SEQ ID NO:2). The new construct was denoted pSEX81ΔL.

Secondly, the pXI encoding sequence was amplified from M13K07 using the 5'-end RE-tagged primer pair pIX_EcoRV/pIX_NheI (5'-ATATGATATCAGAATGAGTGTTT-TAGTGTATTCTTTCGCC-3'/5'-ATATGCTAGCTTATCAT-GAGGAAGTTTCCATTAAACGGG-3') (SEQ ID NO:9 and SEQ ID NO: 10). This PCR fragment was then moved into both the pSEX81 (SEQ ID NO:2), and pSEX81ΔL phagemids on the compatible RE sites, thereby exchanging the pIII encoding region in both and resulting in a N-terminal in-frame pIX fusion of the NcoI/NotI-defined cassette in the original pSEX81(SEQ ID NO:2). The new constructs were confirmed by DNA sequencing and denoted pGALD9 and pGALD9ΔL, respectively. To switch the scFv anti-phOx (SEQ ID NO:11) unit in the various phagemids described above, with the scFv anti-NIP (SEQ ID NO: 3) unit from pSG1, this was done as NcoI/NotI RE defined cassette exchange using standard techniques. All phagemids described herein were introduced into *E. coli* XL1-Blue by electroporation using standard techniques.

Preparation of Phage Particles

Phagemid rescue from *E. coli* XL1-Blue using M13K07 helper phages and virion assembly was monitored by spot titration as described (Welschof et al, PMID: 9050877 and Koch et al, PMID: 11126120).

Phage-Capture Enzyme Linked Immunosorbent Assays (ELISAs)

phOx-BSA or NIP-BSA were absorbed to MaxiSorp™ microtiter plate wells (Nunc, Roskilde, Denmark) at 5 μg/ml in PBS, pH 7.4 overnight at 4° C. The wells were blocked with 2% BSA in PBS (w/v) for 1 h at RT, virion preparations where then added and allowed to react for 1 to 2 h at RT before captured virions were detected with anti-M13-HRP (1:5,000) for 1 h at RT. Between each step, the wells were washed 3× with PBST (PBS/0.05% Tween 20). The wells were developed with TMB soluble substrate, stopped with 1M HCl after 30 min and the absorbance read at $A_{450\ nm}$. To quantify the Ag reactivity as a function of displayed fusion proteins per virion, the ELISA development was stopped before signal saturation was observed for any sample by adding 1M HCl and the absorbency readings transformed according to the following formula: Relative display level=($A_{450\ nm}$/phagemid titer)$\times 10^{12}$.

Spiked phOx-/NIP-BSA Selection

Fresh virion samples were prepared, either with or without 1 mM IPTG induction, PEG precipitated and titrated as described.

The target-specific entity was then spiked into an irrelevant background at a 1:$10^7$ level giving a known diversity of $10^7$, corresponding to a medium sized combinatorial library.

For NIP-BSA selection, the scFv anti-NIP was spiked into the scFv anti-phOx counterpart and vice versa. The initial input was $1\times10^{10}$ $cfu^{ampR}$ resulting in a complexity level of $10^3$ in panning round 1 for all the 12 model libraries.

Briefly, target was immobilized on MaxiSorp™ microtiter plate wells (Nunc, Roskilde, Denmark) in triplicates on the same plate using 100 μl volumes of 1 μg/ml and 0.1 μg/ml for panning round 1 and 2, respectively.

Prior to panning, the wells were blocked with PBSTM for 1-2 h at RT, before 100 μl of the respective pre-blocked (in PBSTM) virion preparations where added and allowed to react for 1.5 h at RT with agitation.

The wells were washed 9× in PBST followed by 5× in $dH_2O$ using a microtiter washer before target bound virions (in triplicate wells) were eluted by either 1) adding 100 μl/well of 100 mM TEA (pH 12) for 5 min at RT followed by neutralization by transfer to fresh well containing 100 μl/well Tris-HCl, pH 6.8; 2) adding 100 μl/well Tryspin/EDTA for 10 min/RT followed by transfer to fresh wells; 3) adding 200 μl/well log-phase ($A_{600\ nm}$ ~0.5, corresponds to ≥$5\times10^7$ cells) *E. coli* XL1-Blue for 30 min at 37° C. with agitation, followed by transfer to 10 ml pre-warmed YT-TAG (2×YT containing 30 μg/ml tetracycline, 100 μg/ml ampicilline and 0.1M glucose) supplemented with M13K07 helper phage at MOI10.

The incubation was continued for 15 min at 37° C. with low agitation followed by 30 min at 37° C. with high agitation. In parallel, the TEA and Trypsin eluted samples were used to infect log-phase *E. coli* XL1-Blue cultures in 9 ml YT-TAG, incubated with low agitation for 15 min at 37° C., before 1 ml YT-TAG supplemented with M13K07 helper phage at MOI10 were added.

The incubation was continued for 15 min at 37° C. with low agitation followed by 30 min at 37° C. with rigorous agitation. All samples were then were centrifuged 3000-g/10 min/RT, the supernatants discarded and the pellets gently resuspended in 10 ml pre-warmed 2×YT containing 100 mg/ml ampicilline and 50 μg/ml kanamycine.

The appropriate samples were supplemented with 1 mM IPTG and all samples incubated ON at 30° C. with rigorous agitation. The day after, the cultures were centrifuged 4000-g/10 min/RT and the supernatant sterile filtered into fresh 15-ml tubes trough 0.2 μm filters.

These supernatants where then channeled into next round of panning as described, using 50 μl volumes/sample corresponding to an input of at least $10^9$ $cfu^{ampR}$/sample. Following the $2^{nd}$ round of selection the virion containing supernatants were channeled into an antigen-specific ELISA as described above.

Results

Figure 2:
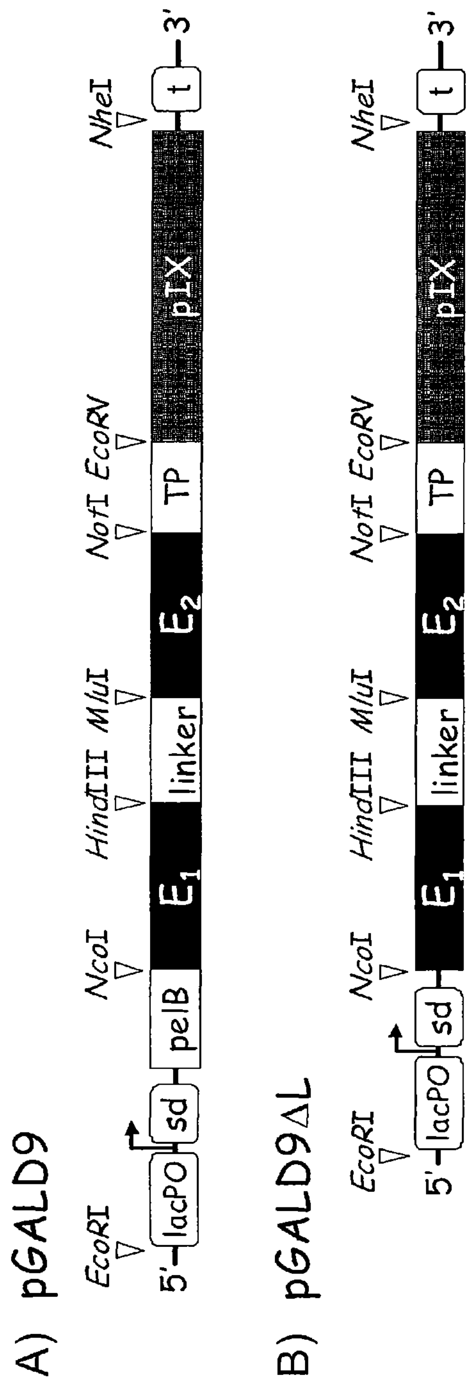

It is known that all the five structural coat proteins of the filamentous phage (fd, M13 and f1) are integral membrane proteins found in the inner membrane of the gram negative host before incorporated into the protruding virion (Endeman and Model, PMID: 7616570). This report also concluded that even though pIX did not allow for any N-terminal fusion modifications, the capsid protein itself was solvent accessible in the intact virion. Both Gao et al (PMID: 10339535 and 12239343) and Khalil et al (PMID: 17360403) have later shown that N-terminal pIX fusion display is allowed when expressed from phagemids and used in combination with signal sequence dependent periplasmic targeting. In these systems, complementation takes place as wt pIX is donated from the helper phage genome upon phagemid rescue. To test if such display also would be allowed without any signal sequence dependent targeting to the periplasm, we have constructed two novel phagemids termed pGALD9 and pGALD9ΔL, allowing for N-terminal pIX display either with or without such a signal sequence, respectively (FIG. 2).

Figure 3:
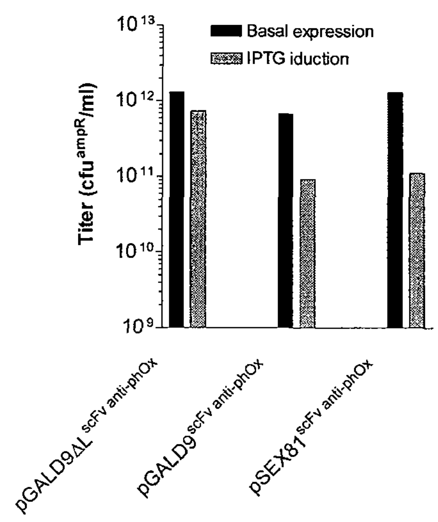
Figure 3:
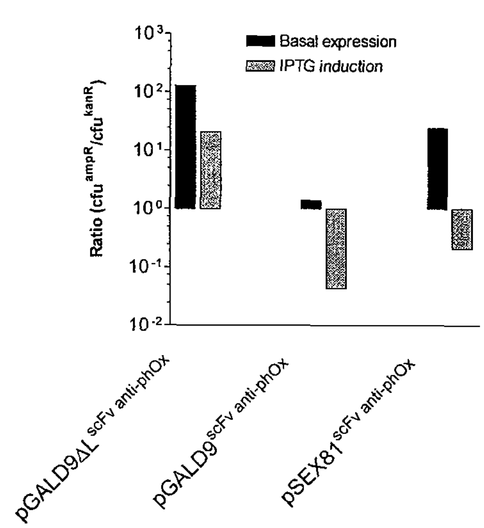
Figure 3:
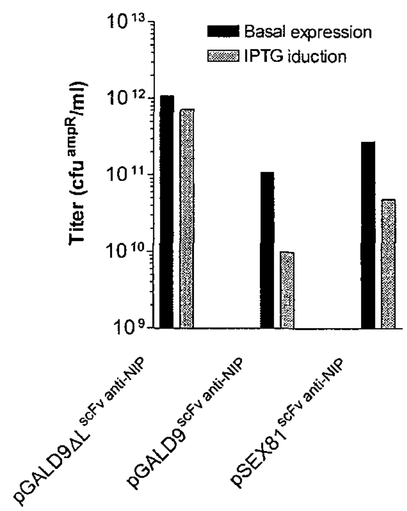
Figure 3:
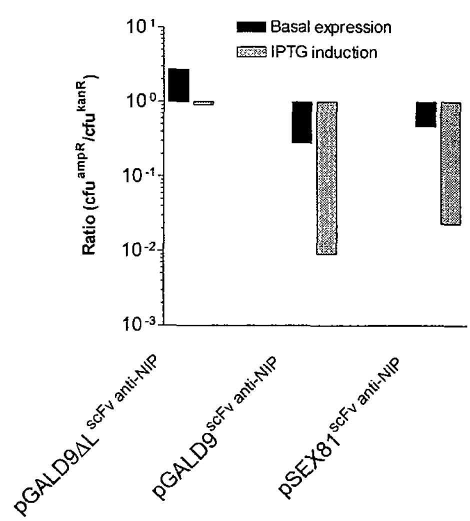

Two different pIX fusions were chosen for analysis using these new phagemids and compared to their counterparts using standard pIII display. Both fusions were antibody fragment scFvs, based on either human antibody variable gene segments and being specific for the hapten conjucate phOx-BSA (scFv anti-phOx), or on murine antibody variable gene segments being specific for the hapten conjucate NIP-BSA (scFv anti-NIP). Notably, the scFv anti-phOx (SEQ ID NO:11) has been selected from a human antibody scFv library and is known to express rather well in *E. coli* (Marks et al., PMID: 1748994). In contrast, it is well known that many murine hybridoma variable genes do not express well in *E. coli* and also when phage displayed (Krebber et al, PMID: 9032408).

pIX display of the scFvs should not interfere with normal virion assembly. We therefore compared the performance of these scFv display phagemids with and without signal sequence and also with standard pIII display (which has an absolute requirement for signal sequenced dependent periplasmic targeting), using standard phagemid rescue and titration as described in materials and methods. (FIG. 3)

The titration result indeed showed that phagemid-containing virions were made in all cases (FIGS. 3A and C). When the scFv fusions are expressed from the lac PO without promoter induction (basal expression), both pIX display versions and the pIII control yield comparable titers for the scFv anti-phOx (FIG. 2A). In contrast, there is a 5- to 10-fold higher titer of the signal sequence independent scFv anti-NIP pIX display in comparison with pIII and signal sequence dependent pIX display, respectively (FIG. 3C). When increased scFv fusion expression was forced upon IPTG induction of the lacPO, it was abut a 10-fold reduction in the titers of both the signal sequence dependent pIX and pIII display. In contrast, there were only minor effects on both signal sequence independent pIX display variants (FIGS. 3A and C). As wt complementation of pIX is present from the helper phage in this system, this finding was both surprising and important, because it shows that the signal sequence dependent pIX and pIII display interferes with the virion assembly process, whereas this effect is only minor in the case with signal sequence independent pIX display even upon IPTG induction. The effect is most prominent when comparing the result from the scFv anti-NIP displayed on pIX with or without signal sequence, where the former exhibits a 100-fold reduction in titer. It is also noteworthy to see that for both scFvs, the virion assembly is as good as or better than pIII when done in the signal sequence independent pIX version.

The core of any combinatorial selection platform is the physical phenotypic-genotypic coupling enabling the retrieval of the genotype through phenotypic selection. If this physical link is compromised or lost, the system is rendered non-functional. Translated to phagemid display this means that it is vital for any selection that it is the phagemid, and not the helper phage genome, that is encapsulated into the virions upon helper phage rescue. As the phagemid and helper phage harbours different antibiotic selection markers, this notion can be easily assessed during infectious titration by computing the phagemid to helper phage ratio based on their respective colony forming units (cfu) resulting from the appropriate selective growth (ampicillin (ampR), or kanamycin (kanR). The ratio should then be above 1 for any efficient downstream selection to be feasible.

When assessing the phagemid to helper phage ratios of the virion preparations described above (FIGS. 3B and D), significant differences between the three display routes were revealed. Using standard virion packaging without promoter induction (basal expression), all three routes are viable for the scFv anti-phOx (FIG. 2B), whereas for the scFv anti-NIP (FIG. 3D) this was only true for the sequence independent pIX variant. Upon promoter induction (IPTG induction), both pIII and signal dependent pIX variants exhibited severe loss of the phenotype-genotype linkage and the effect was most prominent on the scFv anti-NIP fusion. In contrast, this effect was not present (scFv anti-phOx) or mild (scFv anti-NIP) for both signal sequence independent pIX variant. Thus, the results clearly shows that signal sequence independent pIX display harbours a superior phenotypic-genotypic linkage phenotype compared to both standard pIII and signal sequence dependent pIX display.

Figure 4:
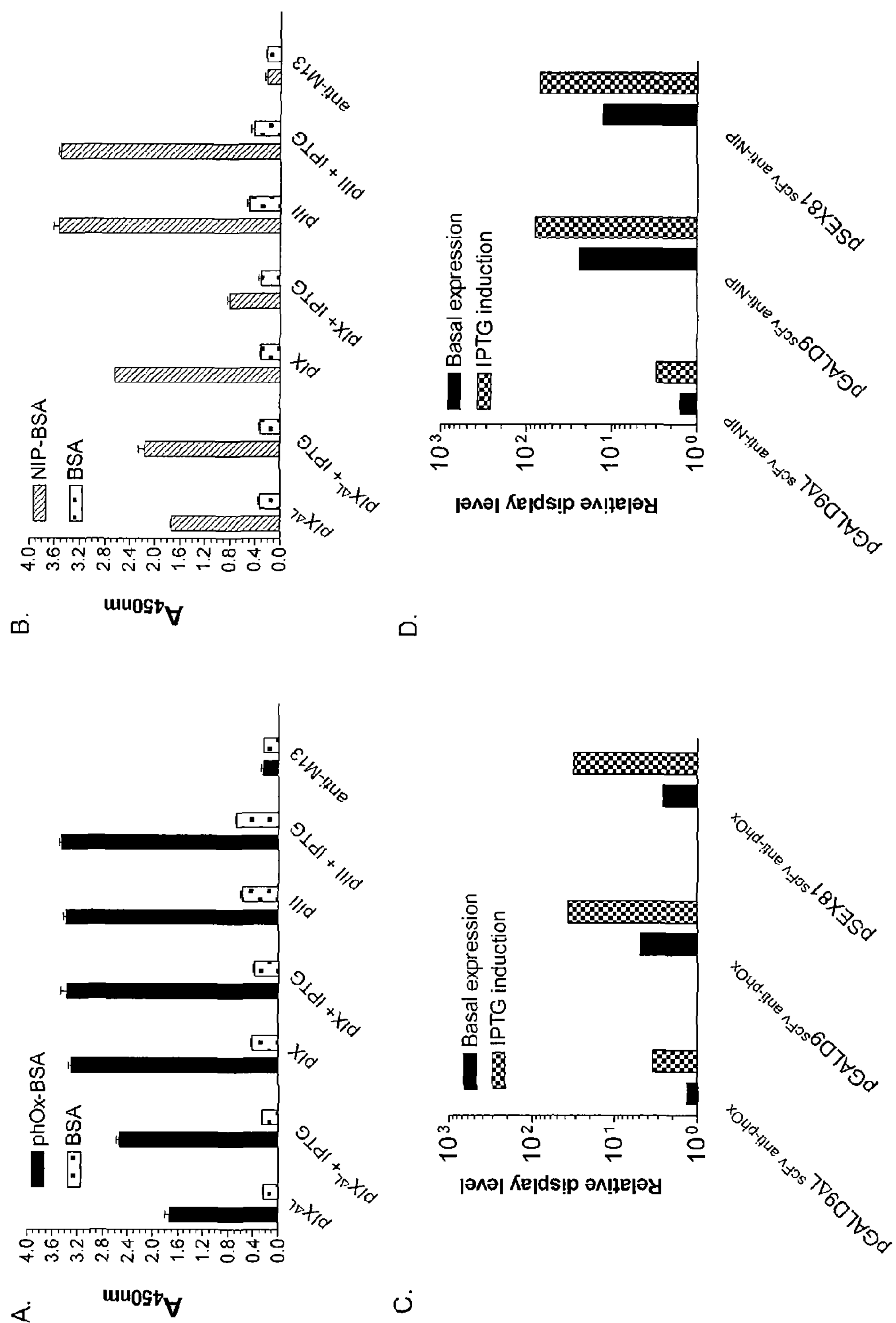

Based upon the samples above, we then assessed the functional scFv display on these virions in an antigen specific ELISA (FIG. 4). The result clearly showed functional scFv display from all three display routes (FIGS. 4A and B). As the samples were not normalized according to phagemid titer, the signal intensities are not directly comparable. Moreover, signal saturation was observed in several samples. To adequately assess functional differences between the three display routes, the relative display levels (functional display units per virion) were determined in a new antigen specific ELISA as described in materials and methods (FIGS. 4C and D). Whereas the display level was comparable between pIII and the signal sequence dependent pIX variant, the signal sequence independent pIX display was significantly lower. This was true for both scFvs and both at basal expression and upon IPTG induction. As expected, all three display routes and for both scFv exhibited higher display upon IPTG induction. It is however, of the outmost importance to see the results for FIGS. 4C and D in light of the ratios given in FIGS. 3B and D). For example, it is clear that both pIII and signal sequence dependent pIX display of the scFv anti-NIP unit exhibits a 10- to 20-fold (basal expression) and ~25-fold (IPTG induction) higher display in comparison with the signal sequence independent pIX counterpart. However, both the two former routes have a very weak or lost phenotypic-genotypic link, which in a combinatorial selection regime would render them non-functional as their genotype will be lost upon phenotypic selection. This effect is also true for the scFv anti-phOx unit, but only upon IPTG induction. Moreover, the display level of the scFv anti-phOx unit in the IPTG induced signal sequence independent pIX variant is comparable to the pIII and signal sequence dependent pIX variants at basal expression. In view of these data it is interesting to see that the only report exploiting the pIX (signal sequence dependent) for scFv display (Gao, PMID: 12239343) always use IPTG induction upon virion packaging, but have not reported the phagemid to helper phage ratios.

Though the scFv format is often used due to favourable expression profiles in *E. coli* (Bradbury and Marks, PMID: 15261570), several reports pinpoints the advantage of lower level display formats, such as e.g. antibody Fab fragments, in retrieving high affinity binders upon affinity selection (de Haard, et al, PMID: 10373423 and Hoogenboom, PMID: 16151404) and Rothe et al (PMID: 18191144).

Thus, even though signal sequence independent scFv-pIX display appears to yield low level display, this may indeed turn out to be highly advantageous when applied for high affinity selection.

Therefore, to assess how signal sequence independent pIX display performs in affinity selection, we compared with conventional pIII display.

Virions were produced in the presence or absence of IPTG induction, and the proteins of interest were either scFv anti-phOx or anti-NIP.

Thus, a total of 4 phage populations were evaluated for the two targets phOx- and NIP-BSA, respectively. In each case, the target specific scFv was mixed with the specificity irrelevant scFv at a ratio of $1:10^7$.

Importantly, the two scFvs do not cross-react. Two rounds of affinity selection were then carried out.

Figure 5:
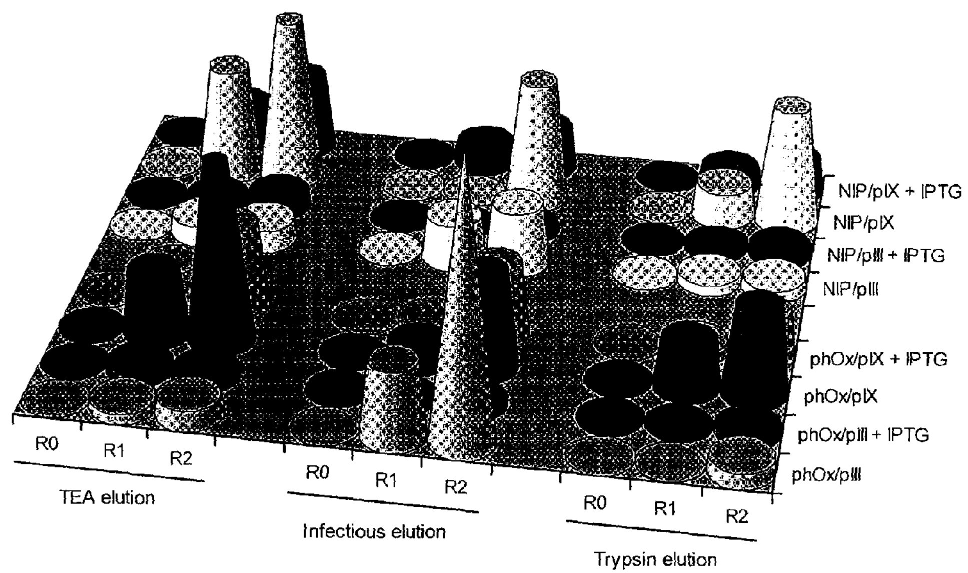

Three different elution strategies were employed; either high pH, proteolytic or direct infection. Enrichment was verified by antigen specific polyclonal phage ELISA following the second round of selection (FIG. 5).

When the protein of interest was displayed on pIX, selection was about equally efficient and in most cases more efficient than when the POI was displayed on pIII. In particular, the standard pIII display route employing high pH (TEA) or proteolytic (trypsin) elution exhibited poor enrichment as compared to pIX.

Selection was more efficient without than with IPTG induction independently of display route and elution conditions, and the negative effect appeared to be most severe for the pIII display route.

Thus, the low display propensity of signal sequence independent pIX did not translate into poor selection. By leaving pIII unaltered and fully solvent exposed, virion rescue following a library selection step may effectively be performed without breaking the virion-target bond, making the elution step redundant and speeding up high through put protocols.

The latter may also facilitate the isolation of high affinity binders, the elution of which may be resistant to a variety of strategies (Balass et al, PMID: 8954559).

REFERENCES

1. Endemann, H. & Model, P. Location of Filamentous Phage Minor Coat Proteins in Phage and in Infected Cells. Journal of Molecular Biology 250, 496-506 (1995) (PMID: 7616570).
2. Gao, C. et al. Making artificial antibodies: A format for phage display of combinatorial heterodimeric arrays. PNAS 96, 6025-6030 (1999) (PMID: 10339535).
3. Gao, C. et al. A method for the generation of combinatorial antibody libraries using pIX phage display. PNAS 2002 Oct. 1; 99(20):12612-6. Epub 2002 Sep. 18 (PMID: 12239343).4. WO/2000/071694. Janda, Kim, D.
5. Khalil A S, Ferrer J M, Brau R R, Kottmann S T, Noren C J, Lang M J, Belcher A M. Single M13 bacteriophage tethering and stretching. Proc Natl Acad Sci USA. 2007 Mar. 20; 104(12):4892-7. Epub 2007 Mar. 13 (PMID: 17360403).

6. Altschul S F, Gish W, Miller W, Myers E W, Lipman D J. Basic local alignment search tool. J Mol. Biol. 1990 Oct. 5; 215(3):403-10 (PMID: 2231712).
7. Baneyx F, Mujacic M. Recombinant protein folding and misfolding in *Escherichia coli*. Nat. Biotechnol. 2004 November; 22(11): 1399-408 (PMID: 15529165).
8. Sambrook et al., Molecular cloning: a laboratory manual. Cold Spring Harbor Laboratory Press.
9. Michaelsen T E, Aase A, Westby C, Sandlie I. Enhancement of complement activation and cytolysis of human IgG3 by deletion of hinge exons. Scand J. Immunol. 1990 November; 32(5):517-28 (PMID: 2125362).
10. Näkelä O, Kaartinen M, Pelkonen J L, Karjalainen K. Inheritance of antibody specificity V. Anti-2-phenyloxazolone in the mouse. J Exp Med. 1978 Dec. 1; 148(6): 1644-60 (PMID: 722243).
11. Kipriyanov S M, Moldenhauer G, Little M. High level production of soluble single chain antibodies in small-scale *Escherichia coli* cultures. J Immunol Methods. 1997 Jan. 15; 200(1-2):69-77 (PMID: 9005945).
12. Norderhaug L, Olafsen T, Michaelsen T E, Sandlie I. Versatile vectors for transient and stable expression of recombinant antibody molecules in mammalian cells. J Immunol Methods. 1997 May 12; 204(1):77-87 (PMID: 9202712).
13. Welschof M, Terness P, Kipriyanov S M, Stanescu D, Breitling F, Dörsam H, Dübel S, Little M, Opelz G. The antigen-binding domain of a human IgG-anti-F(ab')2 autoantibody. Proc Natl Acad Sci USA. 1997 Mar. 4; 94(5): 1902-7 (PMID: 9050877).
14. Koch J, Breitling F, Dübel S. Rapid titration of multiple samples of filamentous bacteriophage (M13) on nitrocellulose filters. Biotechniques. 2000 December; 29(6):1196-8, 2002 (PMID: 11126120).
15. Marks J D, Hoogenboom H R, Bonnert T P, McCafferty J, Griffiths A D, Winter G. By-passing immunization. Human antibodies from V-gene libraries displayed on phage. J Mol. Biol. 1991 Dec. 5; 222(3):581-97 (PMID: 1748994).
16. Krebber A, Bornhauser S, Burmester J, Honegger A, Willuda J, Bosshard H R, Plückthuni A. Reliable cloning of functional antibody variable domains from hybridomas and spleen cell repertoires employing a reengineered phage display system. J Immunol Methods. 1997 Feb. 14; 201(1):35-55 (PMID: 9032408).
17. Bradbury A R, Marks J D. Antibodies from phage antibody libraries. J Immunol Methods. 2004 July; 290(1-2): 29-49 (PMID: 15261570).
18. de Haard H J, van Neer N, Reurs A, Hufton S E, Roovers R C, Henderikx P, de Bruïne A P, Arends J W, Hoogenboom H R. A large non-immunized human Fab fragment phage library that permits rapid isolation and kinetic analysis of high affinity antibodies. A large non-immunized human Fab fragment phage library that permits rapid isolation and kinetic analysis of high affinity antibodies (PMID: 10373423).
19. Hoogenboom H R. Selecting and screening recombinant antibody libraries. Nat. Biotechnol. 2005 September; 23(9):1105-16 (PMID: 16151404).
20. Rothe C, Urlinger S, Löhning C, Prassler J, Stark Y, Jäger U, Hubner B, Bardroff M, Pradel I, Boss M, Bittlingmaier R, Bataa T, Frisch C, Brocks B, Honegger A, Urban M. The human combinatorial antibody library HuCAL GOLD combines diversification of all six CDRs according to the natural immune system with a novel display method for efficient selection of high-affinity antibodies. J Mol. Biol. 2008 Feb. 29; 376(4):1182-200. Epub 2007 Dec. 15 (PMID: 18191144).

The invention claimed is:

1. A phage genome or a phagemid comprising a nucleic acid encoding a fusion protein comprising the filamentous phage minor coat protein pIX fused to an exogenous peptide, wherein the fusion protein does not comprise an N-terminal signal sequence, wherein the filamentous phage minor coat protein pIX comprises a sequence selected from the group consisting of position 1-32, 2-32, 3-32, 4-32 and 5-32 of SEQ ID NO: 1 (MSVLVYSFASFVLGWCLRSGITYFTRLMETSS), wherein the exogenous peptide of the fusion protein is fused directly to the N-terminus of the pIX sequence.

2. The phage genome or the phagemid of claim 1, wherein the exogenous peptide of the fusion protein is selected from the group consisting of an antibody, Z domain of protein A (Affibody), Ankyrin, DARPin, T cell receptor, MHC class I or II, Fibronectin, Anticalins, PDZ-domains, IgNAR, CTLA4, ImmE7, Knottins, avimer, GFP and other gene-encoded biological fluorophores, and fragments of any of the foregoing.

3. The phage genome or the phagemid of claim 1, wherein the exogenous peptide of the fusion protein is a library member.

4. A filamentous phage comprising the phage genome or the phagemid of claim 1.

5. The filamentous phage of claim 4, further comprising a gene encoding wild type pIX and/or the wild type pIX protein comprising SEQ ID NO:1 (MSVLVYSFASFVLGWCLRSGITYFTRLMETSS).

6. The filamentous phage of claim 4, wherein the phage does not comprise a gene encoding wild type pIX and/or the wild type pIX protein comprising SEQ ID NO:1 (MSVLVYSFASFVLGWCLRSGITYFTRLMETSS).

7. The filamentous phage of claim 4, further comprising one or more of the group consisting of a filamentous phage minor coat protein pIII fusion protein, a filamentous phage minor coat protein pVII fusion protein and/or a filamentous phage minor coat protein pVIII fusion protein.

8. A phage display system comprising the phage genome or the phagemid of claim 1 and a helper phage.

9. A kit comprising the phage display system of claim 8.

10. A phage library comprising two or more filamentous phages displaying different proteins wherein at least one of the two or more filamentous phages is the filamentous phage of claim 4.

* * * * *